United States Patent [19]

Barberet et al.

[11] Patent Number: Plant 5,528

[45] Date of Patent: Aug. 6, 1985

[54] CARNATION NAMED LONDESTY

[75] Inventors: Nicole Barberet; Yves Ducloux, both of Antibes, France

[73] Assignee: Laboratoire de Physiologie Vegetale de la Londe, Antibes, France

[21] Appl. No.: 512,730

[22] Filed: Jul. 11, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new carnation cultivar particularly distinguished by the very light chartreuse yellow coloration of its blooms which are borne on long, strong, straight stems and which bloom profusely during the recurrent blooming seasons of Spring and Fall. This plant has a vigorous upright growth habit with moderately abundant foliage and a height averaging about 124 cm. at eight months, which provides rather extra long flower stems making it particularly advantageous for the cut flower market.

1 Drawing Figure

BACKGROUND OF THE NEW PLANT

Our new carnation cultivar is the result of breeding efforts carried on by us at La Londe, Les Maures, France, since 1978, this new plant originating as a seedling produced from our crossing of selected and individually identified plants growing among our stock of plants maintained at La Londe for breeding purposes. This particular seedling was selected by us for propagation and test because of its very unusual flower color and its apparently very favorable growth habit. This discovery plant was reproduced by us at La Londe, by means of cuttings of the parent, and the result of that propagation effort appearing to be very favorable with respect to retention of the novel characteristics of its parent, we continued such propagation through several successive generations and established that the novel and distinctive characteristics of the discovery plant were fully retained from generation to generation and appeared to be firmly fixed.

DESCRIPTION OF THE DRAWING

Our new carnation cultivar is illustrated by the accompanying photographic drawing which has been hand painted to show the true flower color, a typical arrangement of buds and flowers in various stages of opening also being shown.

DESCRIPTION OF THE NEW PLANT

The following is a detailed description of our new carnation discovery based upon observations of greenhouse grown plants made at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 70 J 19 (unpatented).

*Pollen parent.*—Stock Plant No. 340 J (unpatented). These unnamed varieties are individually identified in our permanent records and are maintained for breeding purposes in our collection of carnation plants at La Londe, France.

Classification:

*Botanic.*—Hybrid Dianthus Caryophyllus.

*Commercial.*—Standard Carnation.

Form: Tall, erect bush.

Height: Average; about 124 cm. at eight months.

Main stem:

*Length.*—Less than 15 cm. due to pinching.

Branching character: At least four stems are emitted near the ground.

Growth habit: Vigorous, upright, strong and rigid.

Foliage:

*Quantity.*—Moderately abundant.

*Number of leaves.*—More than 120.

*Leaf size.*—Averaging about 10 cm. long and 1.1 cm. wide at the seventh node.

*Leaf shape.*—Linear with rolled margins and acuminate tips.

*Texture.*—Leathery.

*Color.*—Upper side — 189A and 137C. Under side — 189A and 137C.

*Ribs, veins and rachis.*—Hardly noticeable.

THE BUD

Form: Globular.

Size:

*Diameter.*—Averages about 2.2 cm.

*Length.*—Averages about 3.5 cm.

Rate of opening: About normal for carnations.

Color of petals:

*When sepals first divide.*—About 155B.

*When petals begin to unfurl.*—2C And 2D.

Sepals: The sepals are joined at the lower part and the upper part is of ovate character with sharp pointed apex.

*Number.*—5 To 7 (generally 6). The sepals are hooded over the bud and when flowers open the sepals stand up.

*Color.*—Inside — Greenish White. Outside — 143C and 144C.

*Striae.*—Longitudinal.

Calyx:

*Shape.*—Generally bell shaped.

*Size.*—Medium.

*Splitting.*—Sometimes the calyx does split.

*Aspect.*—Moderately glandular.

Flower stem:

*Length.*—About 78 cm.
*Character.*—Erect and rigid.
*Color.*—189A.

THE FLOWER

Blooming habit: Recurrent and profuse during midseason of Spring and Fall.
Size of bloom: Medium.
*Diameter.*—Averaging about 8.7 cm.
*Depth.*—Averaging about 6 cm.
Borne: Singly.
Shape:
*When bloom first opens.*—High centered.
*When bloom matures.*—Dome shaped.
Petalage:
*Number of petals.*—Averaging about 77.
*Arrangement.*—Imbricated.
*Form.*—Fan-shaped with finely serrated tip end edges.
*Texture.*—Soft.
*Appearance.*—Satiny.
*Color.*—Outer Petal: Body — 2C and 155B. Reverse side — 2 C and 2D. Inside Petal: Body — 2C and 155B. Base — Greenish Yellow. Reverse side — 2C and 2D. All of the petals appear to be streaked with white.
Petaloids:
*Number.*—From zero to 6.
*Size.*—Smaller than the petals.
*Color.*—The same as the petals.
Flower stem:
*Length.*—About 78 cm. (cut at 10th node).
*Character.*—Upright with very good strength.

*Color.*—189A.
Fragrance: Absent or very light.
Persistence: The petals hang on and dry.
Lasting quality:
*As cut flower.*—At least 10 days with vase keeping.
Disease resistance: This variety appears to be resistant to *Fusarium oxysporum* as observed INRA, Antibes, Alpes-Maritimes, France.

REPRODUCTIVE ORGANS

Stamens:
*Number.*—3 To 8 arranged around the pistils.
*Anthers.*—Size: Less than 4 mm. Color: Whitish.
*Filaments.*—Color — Whitish.
Pistils:
*Number.*—3 To 5.
*Styles.*—Color — Yellowish White.
*Stigmas.*—Color — Yellowish White.
Character of ovaries: Lightly ribbed.

When compared with its closest variety "Londorga", our new variety has rounder petals and larger streaks, the streaks being of white color instead of the red color appearing in "Londorga".

We claim:

1. The new and distinct carnation cultivar, substantially as herein shown and described, characterized by the very light yellow and white coloration of its medium sized blooms which are carried on long, straight, stiff stems; and by its advantageous growth habit and abundant production of flowers during its blooming seasons.

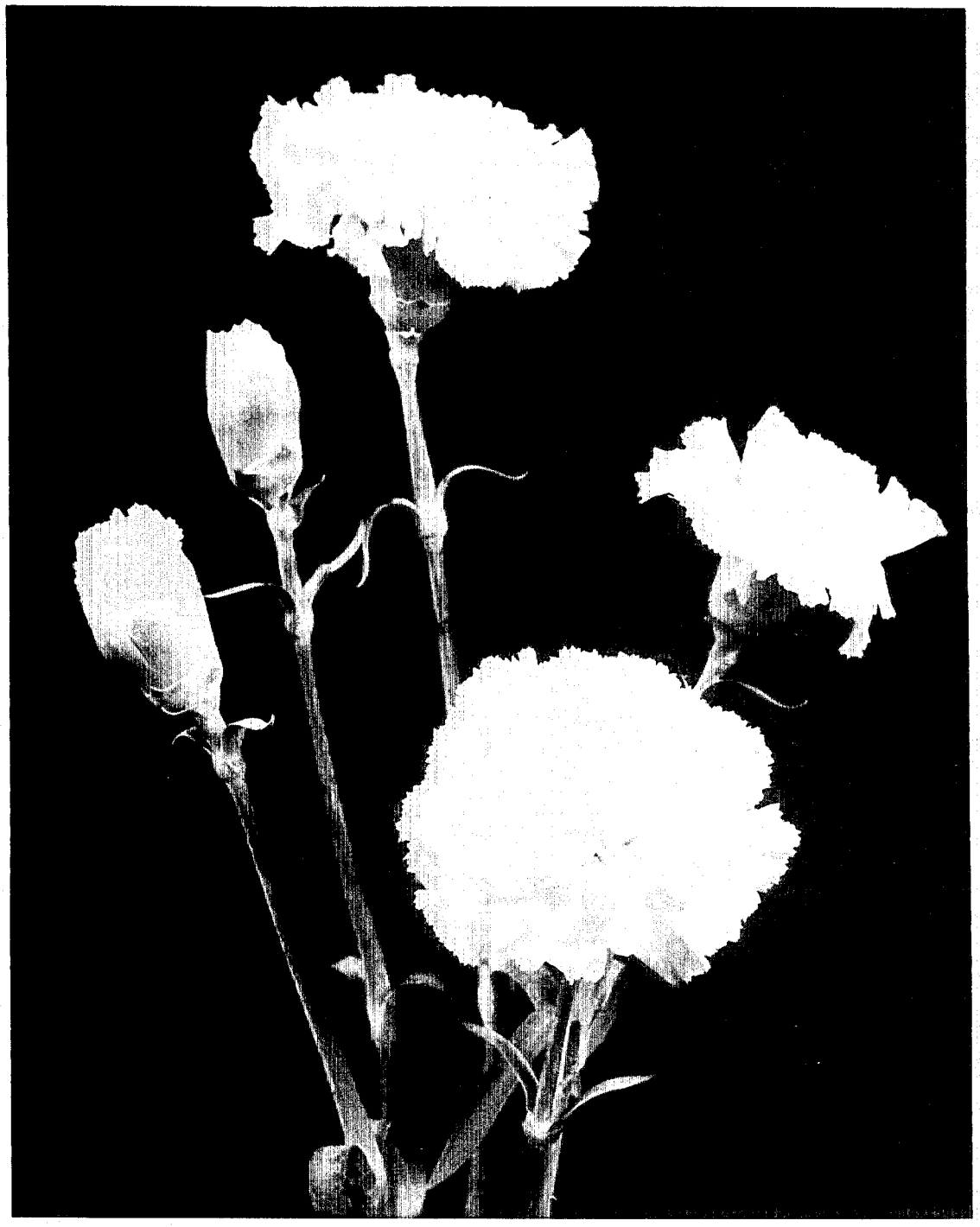

* * * * *